US005560378A

United States Patent [19]
Tiphonnet

[11] Patent Number: 5,560,378
[45] Date of Patent: Oct. 1, 1996

[54] SELF-DISPENSING DENTAL FLOSS APPLICATOR

[76] Inventor: Joel Tiphonnet, Rm 1502, Wing on Centre 111, Connaught Road Central, Hong Kong, Hong Kong

[21] Appl. No.: 342,425

[22] Filed: Nov. 18, 1994

[30] Foreign Application Priority Data

Dec. 1, 1993 [EP] European Pat. Off. ............. 93119373

[51] Int. Cl.$^6$ .................................................. A61C 15/00
[52] U.S. Cl. ...................... 132/325; 132/326; 132/324; 132/327
[58] Field of Search ...................................... 132/323, 324, 132/325, 326, 327

[56] References Cited

U.S. PATENT DOCUMENTS

| 4,495,957 | 1/1985 | Beggs et al. | 132/326 |
| 4,660,584 | 4/1987 | Wofford | 132/325 |
| 4,936,326 | 6/1990 | Eckroat | 132/326 |
| 5,188,133 | 2/1993 | Romanus | 132/325 |
| 5,423,338 | 6/1995 | Hodge et al. | 132/324 |

*Primary Examiner*—Cary E. O'Connor
*Attorney, Agent, or Firm*—Pearne, Gordon, McCoy & Granger

[57] ABSTRACT

A self-dispensing dental floss applicator has a U-shaped elongated housing (1) with two hollow prongs (4a, 4b) at one end and a larger opposite end to contain the locking mechanism and the spool (3) of fresh floss. The locking mechanism composed of a casing (5), two grip pads (7), a spring 8 and a lever (6) with two eccentric friction parts is used to hold the floss in position thus creating the right tension on the floss. After rotating the lever (6) up, a length of floss from the spool (3) is initially pulled through one side of the locking mechanism, spanned through the two prongs (4a, 4b) and then pulled through the other side of the locking mechanism. The used end (16b) of the floss passes through an aperture in the cover (2) and a surplus length thereof is cut off by a cutter. By pulling the floss by hand at the bottom part of the instrument, fresh floss (16A) is spanned between the prongs for use.

9 Claims, 5 Drawing Sheets

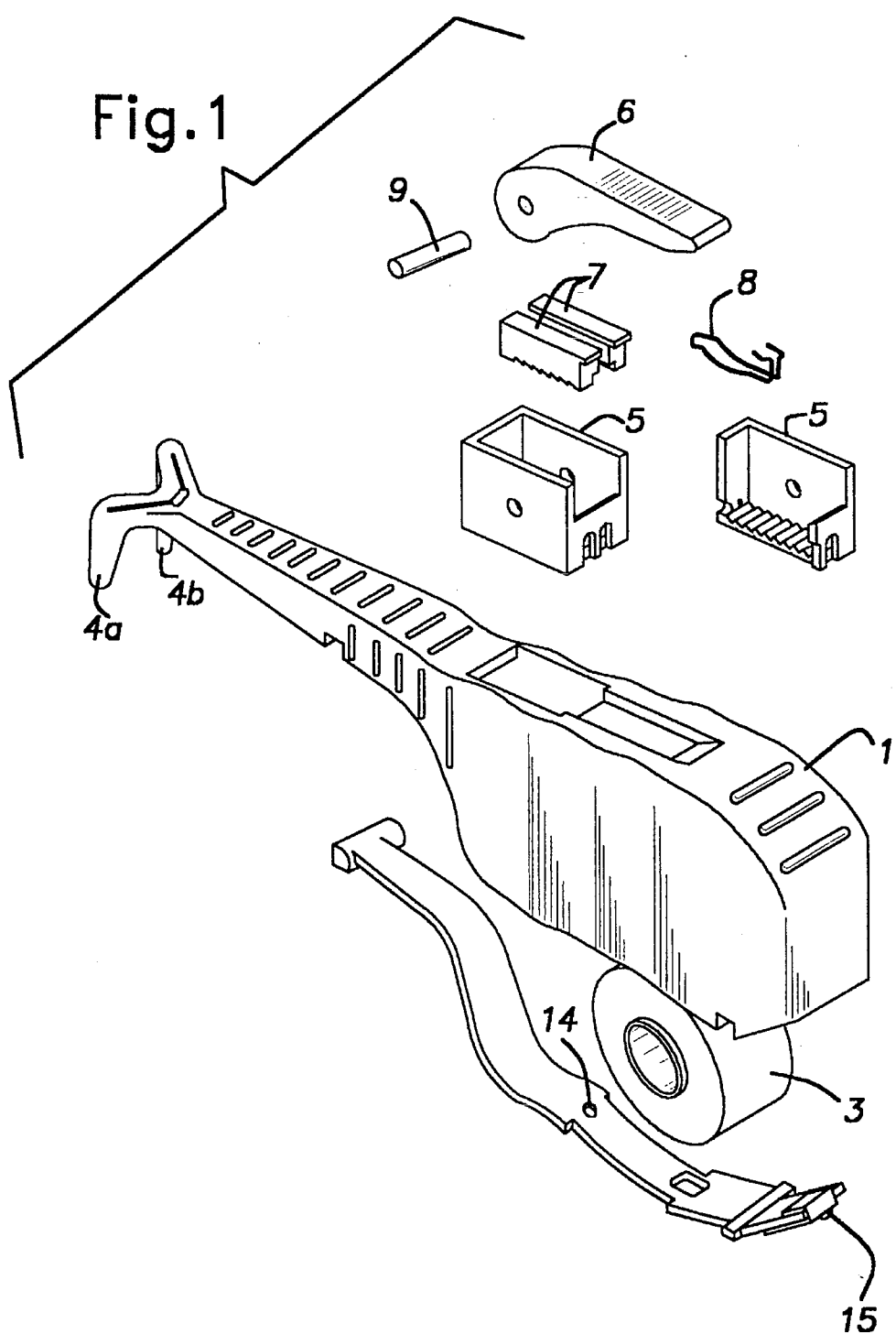

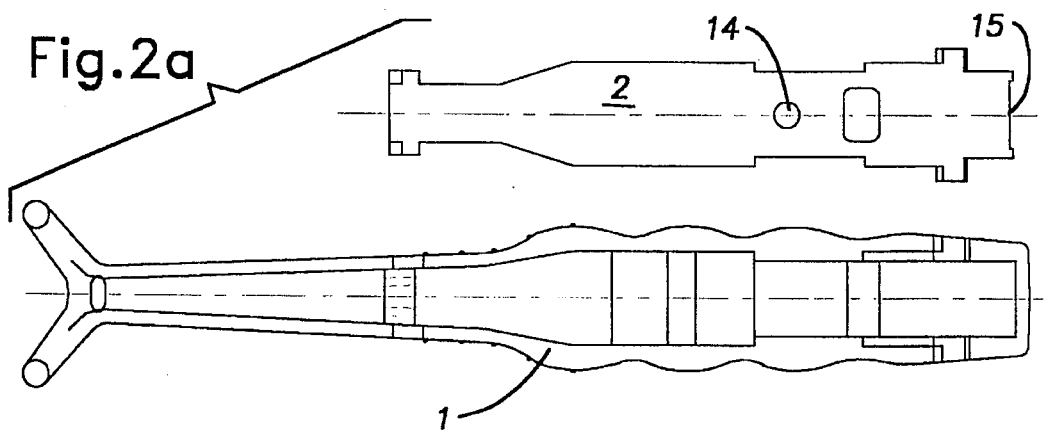
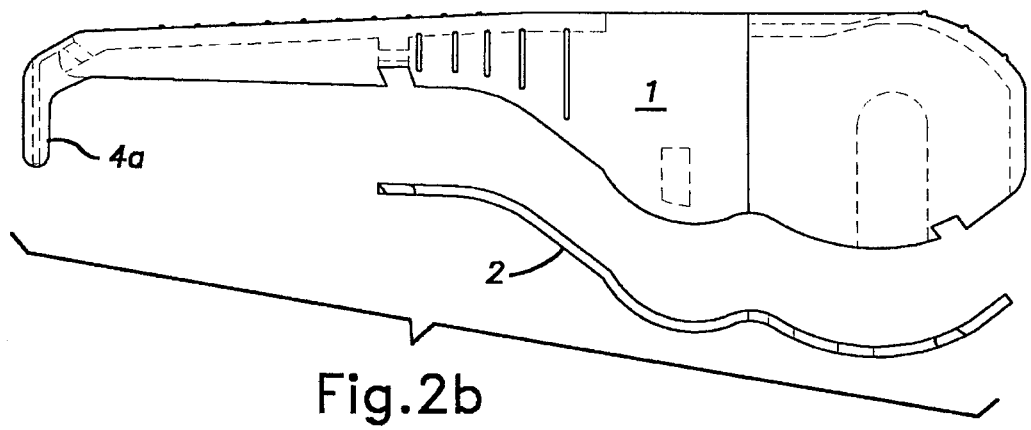
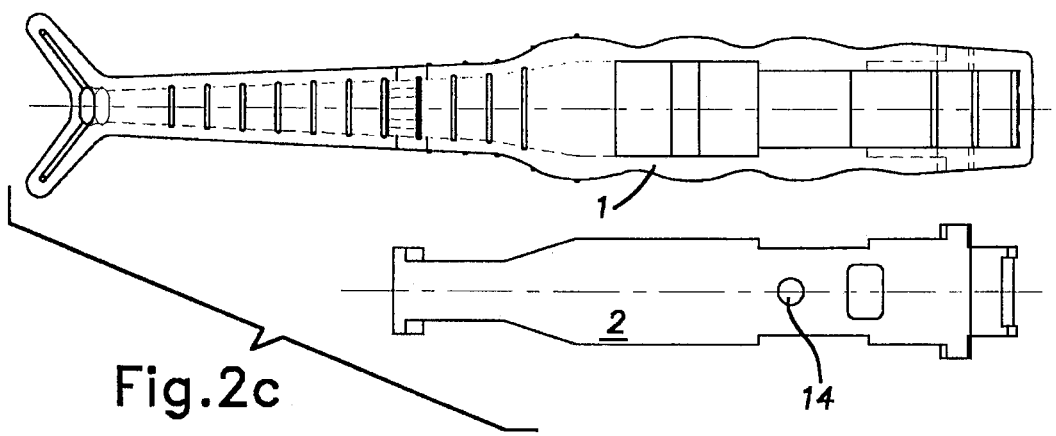

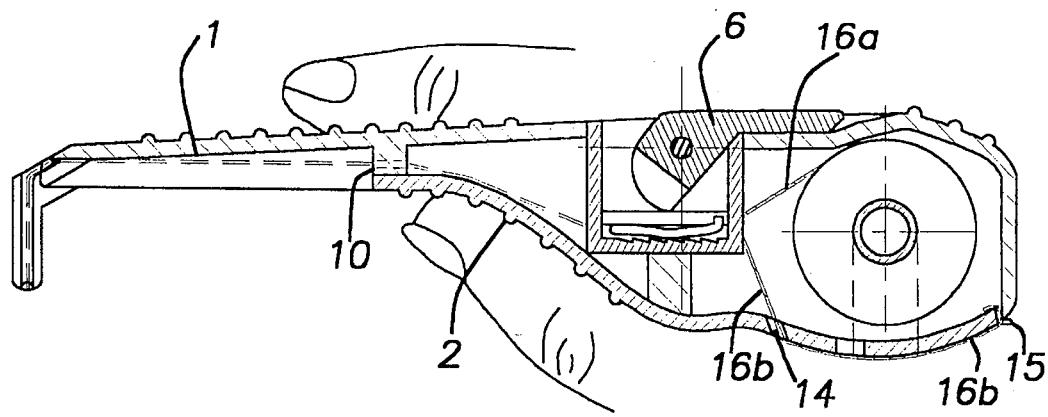
Fig.3a
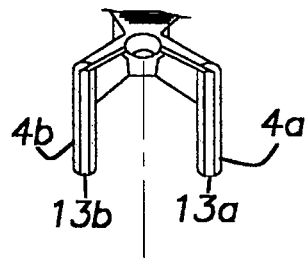
Fig.3b
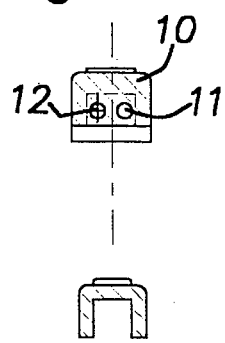
Fig.3d
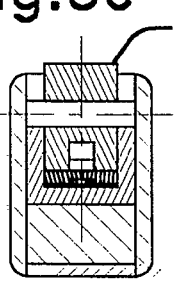
Fig.3e
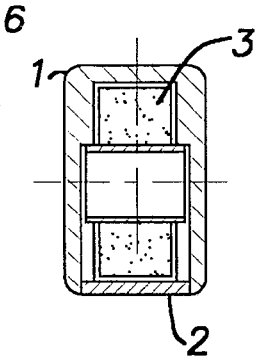
Fig.3f
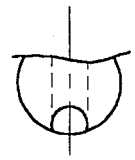
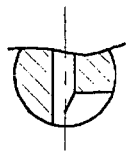
Fig.3c
Fig.3g   Fig.3h

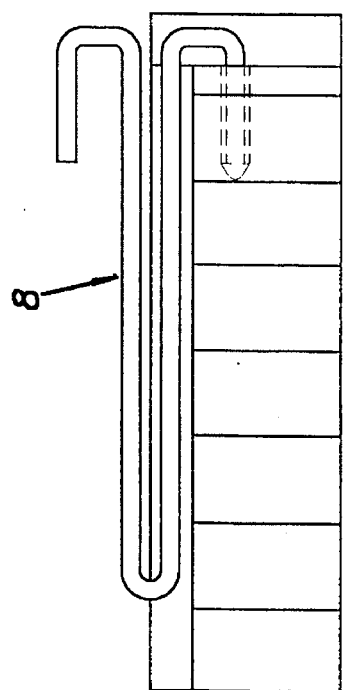
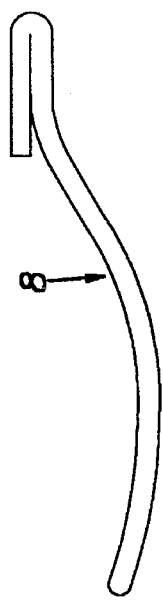
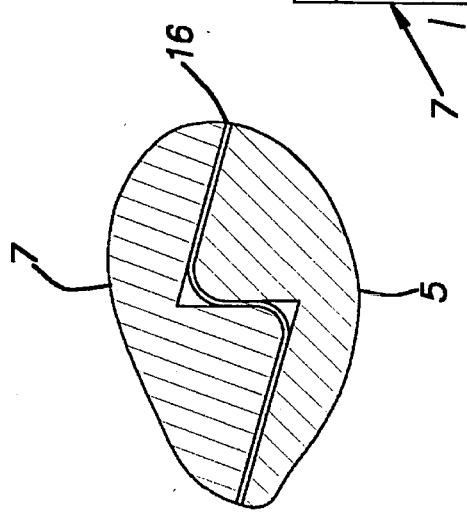
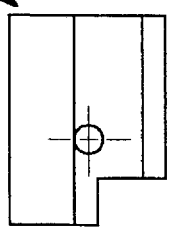
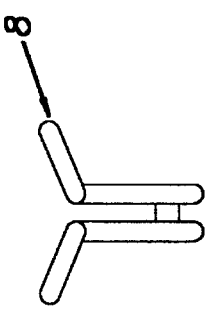

1

SELF-DISPENSING DENTAL FLOSS APPLICATOR

FIELD OF THE INVENTION

This invention relates to a dental floss applicator usable for inserting a string of dental floss between two single teeth and cleaning the gap between these teeth by repeatedly moving the floss back and forth and up and down.

BACKGROUND ART

Dental flossing is recognized by dentists as a necessary and effective part of teeth cleaning and plaque removing. Today, there is not any practical, well-designed device that gives consumers a high level of satisfaction with regard to usage, storage, hygiene etc.

Finger flossing, used by most people, is a very primitive way to floss teeth. It is not hygienic, it hurts gums und fingers. It does not allow an easy reach of rear molars. It is very difficult to control pressure and movement of floss in teeth given the space taken by fingers in the mouth. As result, finger flossing is not an exercise people are keen on, specially children.

Disposable flossers and tooth picks provide an alternative for occasional flossing, but present some disadvantages:

It is impossible to use them for rear molars flossing given that floss is in a longitudinal position (in line with the body).

The floss remains effective for one or two teeth maximum. A normal flossing would require many of those flossers.

The floss tautness rapidly disappears making it ineffective rapidly.

Several different floss holders have been developed to assist in the flossing operation. However, none of them are able to satisfy the requirements of an optimal floss holder. As a result, none have lead to any form of commercialization. They are either too simple and try to replace fingers with devices that require a complex, non hygienic and wasteful reeling of floss. Others are mechanically too complex and would be expensive to manufacture while not giving full satisfaction to users.

DISCLOSURE OF THE INVENTION

It is therefore an object of the invention to overcome these disadvantages and to provide a floss applicator which allows application of the floss in the gap between the teeth in a simple manner without having to grip the floss with the fingers.

According to the invention, a generally U-shaped housing containing a spool of floss at one end thereof and having two hollow prongs at the other end is provided. The floss is fed through the hollow prong and spanned between the free ends of the prongs. The spanned string of the floss is used for cleaning the teeth and then replaced by a new string of floss by pulling the used end of the floss at the bottom part of the housing.

The floss dispenser and applicator according to the present invention is extremely hygienic as there is no contact between fresh floss and the external environment except where it is needed, i.e. between the teeth. Fresh floss is never in contact with fingers and each tooth can be flossed with fresh floss without having to waste long strings of floss. There is no contact between fresh and used floss and used floss is not stored in the instrument but systematically eliminated while using the instrument. This is done by simply pulling the used end of the floss, actioning a lever and using a cutter fitted on the body of the instrument.

BRIEF DESCRIPTION OF THE DRAWINGS

FIG. 1 shows an exploded view of an embodiment of the invention;

FIG. 2a is a bottom view of the housing and body cover of an embodiment of the floss applicator of the invention;

FIG. 2b is a side elevation of the housing and body cover depicted in FIG. 2a;

FIG. 2c is a top view of the housing and body cover depicted in FIG. 2a;

FIG. 3a is a longitudinal sectional view of an embodiment of the floss applicator of the invention;

FIG. 3b is a cross-sectional view of the embodiment depicted in FIG. 3a, taken along line AA;

FIG. 3c is a cross-sectional view of the embodiment depicted in FIG. 3a, taken along line BB;

FIG. 3d is a cross-sectional view of the embodiment depicted in FIG. 3a, taken along line CC;

FIG. 3e is a cross-sectional view of the embodiment depicted in FIG. 3a, taken along line DD;

FIG. 3f is a cross-sectional view of the embodiment depicted in FIG. 3a, taken along line EE;

FIG. 3g is a view of a prong end;

FIG. 3h a cross-sectional view of the prong end depicted in FIG. 3g, taken along line $A_1A_1$;

FIG. 5a is a plan view of the lock mechanism grip pad;

FIG. 5b is an elevational view of the grip pad depicted in FIG. 5a;

FIG. 5c is an end view of the grip pad depicted in FIG. 5a;

FIG. 5d is a detail view of a region of the grip pad depicted in FIG. 5b;

FIG. 5e is an elevational view of a grip pad spring; and

FIG. 5f is an end view of the grip pad spring shown in FIG. 5e.

DETAILED DESCRIPTION OF A PREFERRED EMBODIMENT OF THE INVENTION

Figure 4A:
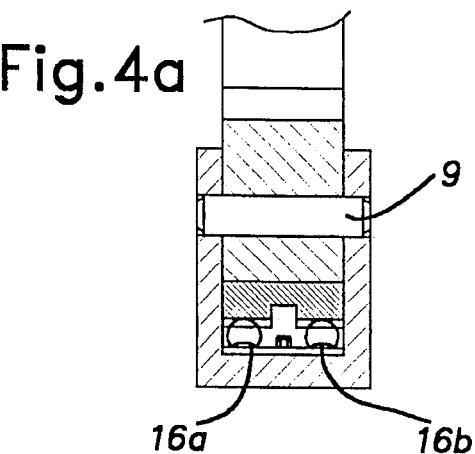
FIG. 4a is a longitudinal sectional view of the locking mechanism in a first stage of operation.

As can be seen in the drawings, the floss applicator according to the invention consists of a generally U-shaped housing 1 with a body cover 2. The space at the larger end of the housing 1 contains a spool 3 of fresh floss and a locking mechanism. This part of the housing is closed by the removable body cover 2. Two hollow prongs 4a, 4b extending parallel to each other are arranged at the other end of the housing.

The locking mechanism consists of a locking mechanism casing 5, a lever 6 with double eccentric, two grip pads 7, and a grip pad spring 8. The lever 6 is rotatably mounted in the casing 5 by an axle 9.

As can be seen in FIGS. 5A to 5F, grip pads 7 are of saw tooth configuration counteracting with the bottom part of casing 5. The saw tooth pattern clamps the dental floss firmly in position without damaging it, thus ensuring the floss tautness being maintained in constant tautness and ensuring a high performance level.

A guiding section 10 with two borings 11, 12 extends in the middle of the housing 1 for passing the fresh and the used floss. As can be seen in FIGS. 3A to 3h, the space containing the spool 3 of fresh floss is substantially closed by the body cover 2 and the guiding section 10.

As can be further seen in FIG. 3b, prongs 4a, 4b are provided with borings 13a, 13b extending axially through them.

Body cover 2 has an opening 14 and a cutter 15 at its rearward end.

Fresh floss 16A is unwound from the spool 3 and guided into the casing 5. From there, it passes through opening 11 into the guiding section 10 and boring 13a in prong 4a. The floss is spanned from the free end of prong la to the free end of prong 4b for use. Used floss 16A is fed back through boring 13b of prong 4b and opening 12 in the guiding section 10. From there, it passes through the casing 5 and the opening 14 in the body cover 2 to the outside.

Figure 4B:
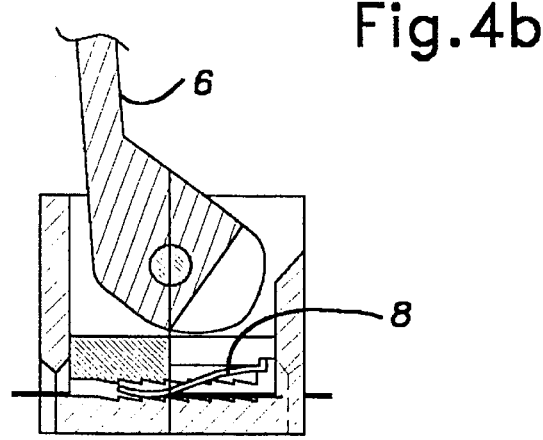
FIG. 4b is a cross-sectional view of the mechanism illustrated in FIG. 4a, taken along lines aa and $a_1a_1$.

For use, the floss is first fed into the applicator in the above manner. For providing a new string of fresh floss spanned between the prongs 4a, 4b, lever 6 is first brought into the position shown in FIGS. 4a and 4b. In this position, under the action of grip pad spring 8, the two grip pads 7 are in their upper position. As such both fresh floss 16A and used floss 16b can move freely. The free end of the floss extending through the hole 14 of the body cover 2 is gripped by the user and pulled until a string of fresh floss is spanned between the prongs 4a, 4b.

Figure 4C:
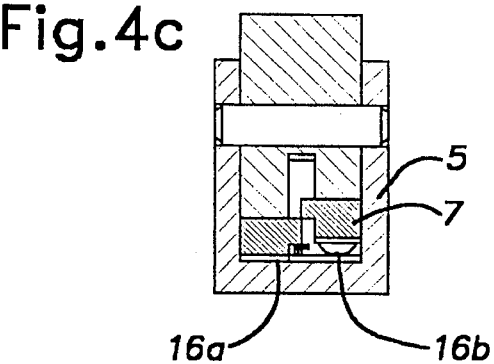
FIG. 4c is a longitudinal sectional view of the locking mechanism in a second stage of operation.
Figure 4D:
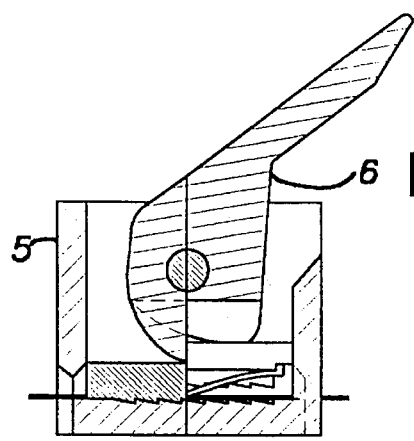
FIG. 4d is a cross-sectional view of the mechanism illustrated in FIG. 4c, taken along lines bb and $b_1b_1$.

Then, lever 6 is brought halfway down into the position shown in FIGS. 4c and 4d. In this position, fresh floss 16a is held by one of the grip pads 7 so that it cannot be pulled any further, while the used floss 16b is pulled to create the right tautness of the floss between the prongs 4a, 4b.

Figure 4E:
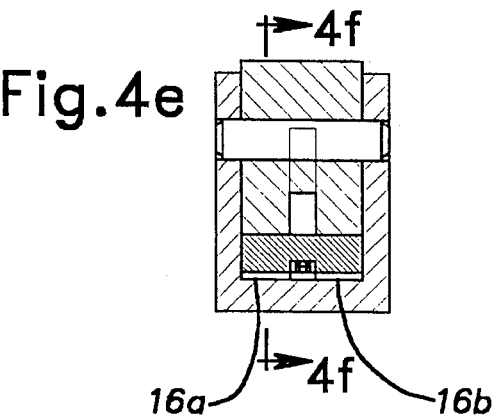
FIG. 4e is a longitudinal sectional view of the locking mechanism in a third stage of operation.
Figure 4F:
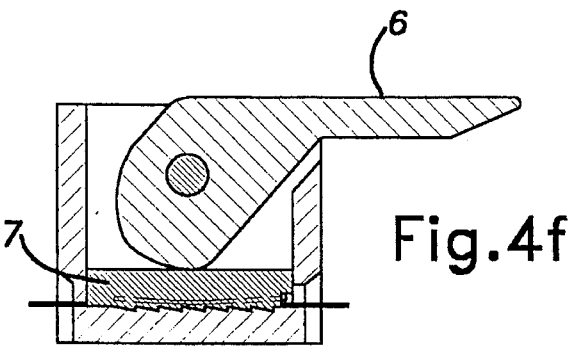
FIG. 4f is a cross-sectional view of the mechanism illustrated in FIG. 4e, taken along line cc.

Finally, lever 6 is brought into the position shown in FIG. 4e and 4f, wherein both grip pads 7 are pressed down to hold both the fresh floss 16A and the used floss 16b. The floss tautness between prongs 4a, 4b is now suitable for teeth cleaning. The surplus length of the used floss 16b extending from the hole 14 is cut off at the cutter 15.

As can be seen from the above description, the floss tautness between the prongs 4a, 4b is constant and the floss is ready to be used between the user's teeth without having to be gripped with the fingers. The used floss 16b is systematically eliminated by using the cutter 15 fitted on the body cover 2, thus avoiding a presence of dirt and germs inside the instrument. A simple action of the lever 6 allows the user to bring fresh floss 16A between the prongs 4a, 4b as often as needed during the teeth cleaning process. The body shape and the presence of ribs give the user full control of the applicator when in use. The spool 3 of floss is replaced by pulling down the body cover 2 and placing the spool axle in a groove existing in the housing 1. The threading of new floss can be made easier by pulling the locking mechanism out of the housing 1 and placing it back once the floss is in place.

On casing 5, four grooves around the entry and exit points prevent squeezing the floss when placing the casing 5 back into the body. The main parts of the applicator, i.e. the housing 1 with the prongs and the body cover 2, can be made from plastic material in an inexpensive process of plastic injection moulding. Alternatively, the instrument can be produced from metal, such as stainless steel or aluminum, especially for professional use by dentists who use such a device frequently. Being of metal, the instrument can be sterilized when necessary.

The shape and size of the applicator according to the invention are such that it can be easily used by all kinds of users: children, adults, left and right-handed people. The flossing of upper and lower teeth is equally easy to perform.

The frontal active floss extending perpendicularly to the floss applicator body and spanned between the specially shaped prongs 4a, 4b allows thorough flossing of rear molars while making it easy for front teeth by turning the instrument on the side of the mouth. The risk of hurting fingers and gums, a frequent result of finger flossing, is completely eliminated.

The floss dispenser and applicator according to the invention is most hygienic in use as there is no contact between fresh floss and the external environment except where it is needed, i.e. between the teeth. Fresh floss is never in contact with fingers and each tooth can be flossed with fresh floss without having to waste long strings of floss. Furthermore, there is no contact between fresh and used floss.

I claim:

1. A self-dispensing dental floss applicator comprising:
   a generally U-shaped housing (1) having a space for a spool (3) of floss at its one end, two hollow prongs (4a, 4b) extending parallel to each other at its other end, a guiding section (10), and a removable body cover (2) defining an opening (14); and
   a locking mechanism (5, 6, 7, 8) disposed in the housing, the mechanism comprising a casing (5), a lever (6) with double eccentric, two grip pads (7), and a grip pad spring (8);
   wherein the floss extends from the spool (3) through the locking mechanism (5, 6, 7, 8), the guiding section (10), the hollow prongs (4a, 4b), back through the guiding section (10), the locking mechanism (5, 6, 7, 8), into the space and to the outside through the opening (14) in the body cover (2).

2. A floss applicator according to claim 1, characterized in that the prongs (4a, 4b) extend substantially at a right angle to the longitudinal extension of the housing (1).

3. A floss applicator according to claim 1 characterized in that the surface of the grip pads (7) facing the bottom of the locking mechanism casing (5) is of saw tooth configuration, counteracting with the bottom of the casing (5) and clamping the floss (16a, 16b) when in locking position.

4. A floss applicator according to claim 3, characterized in that the lever (6) of the locking mechanism can be shifted into three positions, in the first of which (FIGS. 4a, 4b) both fresh floss (16a) and used floss (16b) are freely movable, in the second of which (FIGS. 4c, 4d) fresh floss (16a) is held in position while used floss (16b) can be pulled to create tautness between the prongs (4a, 4b) and in the third of which (FIGS. 4e, 4f) both fresh floss (16a) and used floss (16b) are held in position.

5. A floss applicator according to claim 1 characterized by a cutter (15) for cutting off the surplus length of the used floss (16b).

6. A floss applicator according to claim 5, characterized in that the cutter (15) is arranged at the rearward end of the body cover (2).

7. A floss applicator according to claim 1, characterized in that the housing (1) is provided with gripping ribs.

8. A floss applicator according to claim 1, characterized in that its main parts are made of plastic material.

9. A floss applicator according to claim 1, characterized in that its main parts are made of metal.

* * * * *